(12) United States Patent
Bay

(10) Patent No.: US 8,316,294 B2
(45) Date of Patent: Nov. 20, 2012

(54) METHOD AND APPARATUS FOR ASSISTING THE EVALUATION OF MEDICAL IMAGE DATA

(75) Inventor: Susanne Bay, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 810 days.

(21) Appl. No.: 12/232,524

(22) Filed: Sep. 18, 2008

(65) Prior Publication Data

US 2009/0094513 A1    Apr. 9, 2009

(30) Foreign Application Priority Data

Sep. 28, 2007  (DE) .......................... 10 2007 046 704

(51) Int. Cl.
*G06F 17/27* (2006.01)
*G06F 17/30* (2006.01)
*G06K 9/20* (2006.01)

(52) U.S. Cl. ......... 715/243; 715/231; 715/273; 382/128
(58) Field of Classification Search .................. 715/231, 715/243, 273; 382/128
See application file for complete search history.

(56) References Cited

U.S. PATENT DOCUMENTS

| | | | |
|---|---|---|---|
| 6,360,116 B1 | 3/2002 | Jackson et al. | |
| 6,754,376 B1 * | 6/2004 | Turek et al. | 382/131 |
| 6,785,410 B2 * | 8/2004 | Vining et al. | 382/128 |
| 6,904,161 B1 * | 6/2005 | Becker et al. | 382/128 |
| 7,155,043 B2 * | 12/2006 | Daw | 382/128 |
| 2003/0016850 A1 * | 1/2003 | Kaufman et al. | 382/128 |
| 2005/0100136 A1 * | 5/2005 | Kawatsu | 378/207 |
| 2005/0228250 A1 * | 10/2005 | Bitter et al. | 600/407 |
| 2007/0127793 A1 * | 6/2007 | Beckett et al. | 382/128 |

FOREIGN PATENT DOCUMENTS

EP    1406203 A2    4/2004

* cited by examiner

*Primary Examiner* — Laurie Ries
*Assistant Examiner* — Ariel Mercado
(74) *Attorney, Agent, or Firm* — Harness, Dickey & Pierce, P.L.C.

(57) ABSTRACT

A method for assisting the evaluation of medical image data is disclosed. In at least one embodiment of the method a current layout is displayed which presents a particular arrangement of image series or individual images which are generated using one or more data records. Further, at least one executable work step is displayed which has at least one associated further layout, wherein the further layout involves at least the arrangement being changed, and, in particular, other information from the data records or other data records are used for generating the image series or images. Finally, a check is automatically performed to determine whether execution of the displayed work step requires a layout change in which the current layout is replaced by the further layout, or the current layout can be retained.

19 Claims, 1 Drawing Sheet

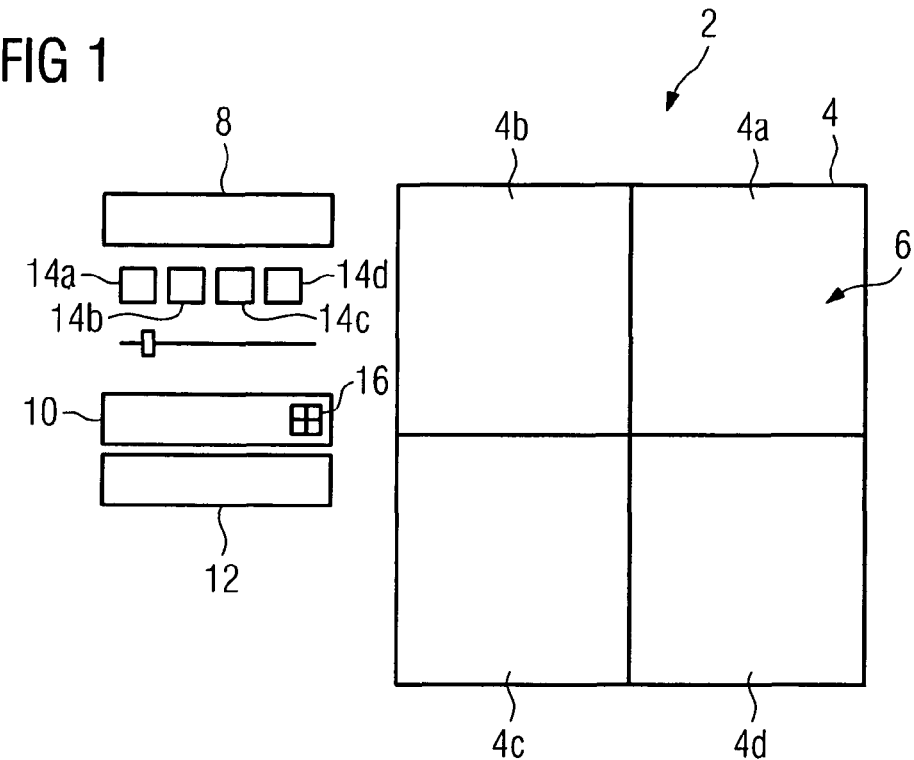

METHOD AND APPARATUS FOR ASSISTING THE EVALUATION OF MEDICAL IMAGE DATA

PRIORITY STATEMENT

The present application hereby claims priority under 35 U.S.C. §119 on German patent application number DE 10 2007 046 704.6 filed Sep. 28, 2007, the entire contents of which is hereby incorporated herein by reference.

FIELD

Embodiments of the invention generally relates to a method for assisting the evaluation of medical image data and/or to an apparatus for performing the method.

BACKGROUND

In medical diagnostics, different imaging methods are used to be able to detect anomalies in the body of a patient. Examples of such methods are x-ray diagnostics, which also includes computed tomography (CT), positron emission tomography (PET), magnetic resonance tomography (MRT), etc. An earlier practice for visual analysis of x-ray pictures was to hang the x-ray images printed on transparencies on a light wall. Nowadays, the light wall is replaced by a computer whose screen is used to display the data records obtained using the imaging method. A doctor's work is also assisted by a suitable software program which can be used to edit and evaluate the image data records electronically.

When analyzing and evaluating the examination images, it is of great importance that the doctor keeps his attention on particular images or areas of the images. In this context, the software programs for displaying and editing the examination images have functions, subsequently called work steps ("tasks"), whose execution requires particular graphical and data-related requirements to be met, so that the image data are visually displayed in a defined arrangement, in this case referred to as a layout. These requirements may be different for the different work steps, so that a change in the layout is unavoidable as soon as the next work step is executed.

SUMMARY

In at least one embodiment of the invention, a treating doctor evaluating medical pictures is provided with assistance such that he can focus his visual attention on particular pictures for as long as possible.

In at least one embodiment of the invention, a method for assisting the evaluation of medical image data comprises:
  a current layout is displayed which presents a particular arrangement of image series or individual images which are generated using one or more data records,
  at least one executable work step is displayed which has at least one associated further layout, wherein the further layout involves at least the arrangement being changed, and, in particular, other information from the data records or other data records are used for generating the image series or images, and
  a check is automatically performed to determine whether execution of the displayed work step requires a layout change in which the current layout is replaced by the further layout, or the current layout can be retained.

In the case of computer-aided visualization and editing of image data records which have been obtained by way of one or more medical imaging methods, the medical pictures are displayed in different areas of the screen, in this case called segments. The doctor or the user of the software assisting the evaluation can then select or mark particular pictures which are of special interest to him. The displayed arrangement of medical pictures is referred to as a layout. A layout may contain one or more images from an image series. However, a layout may also be made up of images from a plurality of image series, e.g. of images which have been taken at different times, or images which have been obtained using different imaging methods, such as CT and PET.

By way of example, a layout includes sectional pictures of different body regions in the sagittal direction, transverse direction or frontal direction. Furthermore, the layout may alternatively or additionally contain coronal or sagittal reconstructions. In summary, a layout optionally comprises different images for the medical method used to obtain the image data records, different images for the editing and presentation of the information from a data record, or images of different body regions. Suitable selection of the layout allows the user to focus on particular especially relevant pictures so that he can perform the evaluation of these pictures in a target-oriented fashion.

For evaluating the diagnosis pictures, the software also has different work steps implemented in it, each work step having an associated suitable layout which meets the requirements for performance of the work step. Normally, there is therefore usually a layout change following execution of the work step. In this case, a layout change is not understood to mean solely changing the presentation with regard to colors, sizes or perspective, but rather the arrangement of the images is changed or the image data records are used to generate new images or image series which are presented as a substitute for or in addition to the already displayed images.

To obtain maximum constancy in the presented data records, the proposed method of at least one embodiment involves automatically checking whether, on the basis of a current layout, the execution of a particular work step requires the layout to be changed or may have the current layout retained. That is to say that a layout switch is context-sensitive or context-dependent. Such a check provides the opportunity for the user or alternatively the software to make a decision about whether or not the work step is executed under the present circumstances.

In line with at least one development of the method, a plurality of workflows for different evaluations of the image data are provided for selection by a user. A workflow is a defined sequence comprising a plurality of work steps and represents a simplification for the evaluation or editing of data, since the procedure is stipulated and hence target-oriented. An example of such a workflow for the evaluation of medical image data is the determination of the volume of a tumor. In this case, the work steps comprise identification of the structure, determination of the outlines, segmentation and evaluation of the volume.

The user's work is also simplified by virtue of, in line with another preferred development of at least one embodiment of the method, the selected workflow being taken as a basis for displaying particular work steps. The work steps are therefore presented in workflow-dependent or workflow-sensitive fashion: not all the work steps are provided, but rather only those which can be used for editing or evaluating the image data within the chosen workflow.

As already discussed, each work step has at least one associated layout which is displayed when the work step is executed. In addition, each work step preferably has associated tools for editing the image series or the individual images. When the work step is executed, the correct tools which are suitable for editing the image data and hence the layout are therefore also specified straightaway. The work step is therefore used to link the tools to the layout.

Appropriately, the layouts are associated with the work steps automatically using a stored table. The table is part of the software program for evaluating the medical image data and may additionally also comprise the association of the tools with the individual work steps.

For the check, an apparatus is provided which includes a control unit and also a display element for presenting the layout. The control apparatus preferably checks whether the graphical and data-related requirements for execution of the work step are met, even if the layout is retained, and displays the result of the check particularly as an indicator. The method of at least one embodiment therefore provides the user of the software program with a high level of transparency concerning what will happen following activation of the work step. The result is displayed particularly in the form of an indicator or a symbol which is associated with the respective work step. By way of example, such an indicator may be used to mark only work steps whose execution will result in a layout switch. The absence of an indicator for a work step would indicate that the layout settings are retained for the activation of this work step. It is also possible for two different indicators to be displayed depending on whether or not the execution of the work step prompts retrieval of a new layout.

In accordance with one example variant, a work step has a plurality of admissible or associated layouts and these are assessed automatically in respect of their suitability for the work step on the basis of context. This means that when there are a plurality of layouts which are associated with a work step, on the basis of the current layout, a check is first of all performed to determine whether this layout can be retained, i.e. whether one of the associated layouts corresponds to the current layout. This layout is then assigned the highest ranking. When assessing the layouts, it is also possible to take account of how often a layout occurs for the work steps which the current workflow comprises.

In accordance with another example variant, a check is automatically performed to determine whether the execution of a work step requires, is recommended to involve or may optionally involve a layout change. For this, particularly the result of the context-related assessment is taken into account. For recommended or optional layout change, the user himself can decide whether the current layout is retained or another, permitted layout is better for evaluating the image data and needs to be used.

The visual result of the check is improved in that, advantageously, depending on whether the execution of a work step requires, is recommended to involve or may optionally involve a layout change, the indicator is displayed in different forms, particularly in different colors. By way of example, a red indicator may indicate an urgently required layout change, a yellow indicator may indicate a recommended layout change and a green indicator may mean that the current layout is retained even after execution of the work step.

Preferably, the current layout is automatically replaced by the further layout only if a layout change is assessed as being required for the execution of a work step. This is done particularly when the work step to be executed has only a single layout associated with it and it is not the current layout. In the case of a recommended or optional layout change, the user in particular decides whether the current layout is retained. Alternatively, a layout change assessed as "recommended" can also take place automatically.

Preferably, the current layout is automatically replaced by the further layout if the current layout is not one of the layouts which are admissible for the step which is to be executed. When there are a plurality of admissible layouts, particularly the software program sets the layout with the highest ranking.

Appropriately, if a plurality of layouts are admissible for the work step which is to be executed, a selection list with associated layouts is displayed. This is done particularly when the current layout is not among the layouts associated with the work step and another layout needs to be selected by the user.

In line with another example refinement, the current layout can be set manually by a user. For reasons of simplicity when evaluating the image data records, the user is provided with the option of changing the current layout manually. By way of example, the user can add new data to a segment or can change the orientation of the presented data records. Particularly in the case of user-controlled setting of the current layout, it is of great importance to retain the optimized layout with as few changes as possible when executing a subsequent work step. For this reason, a check to determine whether the activation of the work step involves a layout change taking place is particularly meaningful and is of great advantage for visually displaying the medical image data with as little interference as possible.

Any addition or removal of an object from the current layout or any reorientation of the data records changes the relationship between the current layout and the further layout which is associated with the work step. So that the user is always provided with current information regarding whether the execution of the displayed work step requires a layout switch, a manual change to the current layout preferably involves the check being performed automatically and the displayed result being updated.

Advantageously, the execution of the work step involves the result of the check being taken as a basis for essentially retaining or modifying the settings for the current layout. If the result of the check is that the current layout meets the requirements which are necessary for a specific work step, the execution of this work step involves the current layout being retained. Only if the current layout is not compatible with the visual display requirements of the work step is it replaced by the new layout for the execution of the work step. The method of at least one embodiment is therefore used to retain the current layout settings for as long as possible, so that the visual perception of the user is disturbed as little as possible during the evaluation.

Another advantage is that when there are a plurality of work steps the order for performing the work steps is stipulated by the user. In this case, the user is given the freedom to specifically avoid a layout change by deciding himself which of several possible work steps is executed next. If the present layout, for example, involves the indicator indicating that the layout is changed for the execution of a work step A and the layout is not changed for the execution of another work step B, the user can select execution of the work step B first and execution of the work step A only afterwards.

At least one embodiment of the invention is directed to an apparatus for performing the method based on one of the preceding embodiments. The advantages and preferred refinements which are specified for the method can be transferred to this apparatus, mutatis mutandis.

BRIEF DESCRIPTION OF THE DRAWINGS

An example embodiment of the invention is explained in more detail with reference to the drawings, in which:

FIG. 1 shows a user interface for performing a workflow, and

FIG. 2 shows a table with different work steps which have associated layouts and tools.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a user interface 2 which contains a segment block 4 for displaying a current layout 6 and also a plurality of work steps 8, 10, 12 for clicking on. In this example embodiment, the segment block 4 comprises four segments 4a-d, with one or more pictures of an image series being presented in each of the segments 4a-d. The combination of displayed medical image data in the different segments 4a-d forms the current layout 6. In this case, an image series may be a CT data record, for example, which comprises sectional pictures of a body region from a particular direction. In addition, pictures from the current examination and pictures from an earlier examination can be displayed in different segments 4a-d for comparison purposes.

Furthermore, it is possible for the layout 6 to contain pictures which have been obtained using different imaging methods, e.g. a CT data record next to a PET data record. The drag-and-drop method allows a user to drag individual images or image series, so that he arranges the data records in an order which is optimum to him. In addition, it is possible for the user to add or delete images and image series, and also for him to change the orientation of the images by way of simple manipulations.

To assist the evaluation, other buttons besides the segment block 4 containing the current layout 6 are provided which represent the different work steps 8, 10, 12. In the example embodiment shown, the first work step 8 is the active work step already executed, with which the current layout 6 is associated. To add to the work step 8, a plurality of editing tools 14a-d are also presented graphically. Clicking on one of the work steps 8, 10, 12 allows the following functions to be executed, for example:
view current CT and PET data records;
register two data records, that is to say overlay and associate the two data records in order to be able to locate a tumor and determine its volume;
compare the current data records with earlier pictures.

In the example embodiment shown in FIG. 1, the activation of the first work step 8 involves registration between a CT data record and a PET data record, which involves an association being produced between the data records, so that a tumor visually displayed in the PET pictures can be located in the patient's body by way of the CT data record and its volume can be calculated. In this case, the editing tool 14a may be what is known as a "visual alignment" tool, which the user uses to drag the pictures over one another on the screen using the mouse. Another tool 14*b* may be an "automatic registration" tool, for example, whose operation prompts the data registration to be performed. By way of example, the other tools 14*c*, 14*d* can be used for other manual or automatic adjustments to the registered data records.

To simplify the evaluation of the medical pictures, the user himself can make changes to the current layout. The performance of the work steps 10, 12 is linked to particular requirements which need to be met regarding the layout. The software program for visual display and editing of the medical image data, part of which is the user interface 2 shown in the figure, is used to automatically check whether the requirements of the further work steps 10, 12 are met by the current layout. In addition, such a check is performed every time the user has manually changed the settings for the current layout 6.

The result of the check is displayed in the form of an indicator 16 which, in the example embodiment shown, can be presented within the button for the other executable work steps 10, 12. In the example embodiment shown in the figure, the indicator 16 shown for the work step 10 indicates that the execution of this work step 10 requires or automatically involves a layout change. The absence of such an indicator 16 in the button 12 is an indication that the current layout 6 meets the visual requirements of the work step 12, so that the execution of this work step 12 does not involve a layout change.

Alternatively, each of the work steps 8, 10, 12 may be flagged by an indicator 16, the indicators 16 being in different forms depending on whether the execution of the respective work step 8, 10, 12 prompts a layout change. The indicator 16 can be assigned different colors, for example. By way of example, the indicator 16 may be red, yellow or green depending on the situation. A red indicator would mean that a layout change is required for the execution of the step. If the current layout 6 can be retained, a yellow or a green indicator 16 would, by contrast, mean that a layout change is recommended or only optional, respectively.

The indicator 16 means that, even before he has executed the respective work step 10, 12, the user knows whether or not this will result in a layout change. This gives the user other freedoms and control options for presenting and manipulating the image data on the user interface 2, since the assisting software program can be used by the user to stipulate the order in which the work steps 8, 10, 12 are executed. In the specific case, the user can decide to execute the work step 12, which does not involve a layout change, first, so that the user's visual attention is not diverted upon every further work step by virtue of his manual settings being replaced by the basic settings of the program.

The table 18 in FIG. 2 contains two workflows WF1 and WF2 which respectively comprise a plurality of work steps A1 to A6. Each of the work steps A1-A6 has an associated layout L1 to L5 which is displayed when the respective work step A1-A6 is executed. Furthermore, each work step A1-A6 has different associated tools T1 to T12 for editing the image segments 4*a-d* presented on a display element (not shown in more detail).

A work step A1-A6 may also have a plurality of associated layouts L1-L5. Such an association can be monitored using the simplified table in FIG. 2. In cases in which a plurality of layouts L1-L5 are suitable for executing the work step A1-A6, e.g. when a layout change is recommended, the user can select the desired layout L1-L5 particularly by clicking on the indicator 16.

As can be seen from the table 18, the performance of the first workflow WF1 involves a first work step A1 with an associated layout L1 being loaded on the basis of context, the displayed images being able to be edited using the tools T1, T2 and T3. Since the next work step A2 has the same layout L1 associated with it, execution thereof does not involve the original layout L1 being changed. When the third work step A3 is executed, the layout change can be made optionally, the user can retain the current layout L1 or can change it over to another L2. If the layout L1 has been retained, a layout change is likewise also optional when the work step A4 is executed. If the user has decided upon the layout L2 beforehand, however, the layout L2 needs to be replaced by L1 or L3 when A4 is executed.

The workflow WF2 requires a layout change when changing from A1 to A4, since the work step A4 does not have the original layout L1 associated with it. For step A4, the layout L5 is flagged as being recommended, since this layout is also associated with the further work steps A5 and A6 of the work flow WF2. If the user wishes to select L5, a layout change from A4 to A5 and from A5 to A6 is optional.

Starting from A1, the user can nevertheless decide to execute the step A6 first so that the layout L1 is retained. For A6, there can be a layout change to L5, which is then no longer changed when the remaining work steps A4 and A5 are executed.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for assisting the evaluation of medical image data, comprising:
- displaying a current layout which presents an arrangement of at least one of an image series and individual images which are generated using one or more data records;
- displaying at least one executable work step which has at least one associated further layout, wherein the further layout involves at least the arrangement being changed;
- performing a check to determine whether execution of the displayed at least one executable work step requires a layout change in which the current layout is replaced by the further layout, or whether the current layout is to be retained, a result of the performed check is displayed as an indicator, the indicator indicating if the layout change is required;
- wherein, depending on whether the execution of a work step requires, is recommended to involve or may optionally involve a layout change, the indicator is displayed in different forms; and
- wherein the current layout is automatically replaced by the further layout if a layout change is assessed as being required for the execution of a work step.

2. The method as claimed in claim 1, wherein a plurality of workflows for different evaluations of the image data are provided for selection by a user.

3. The method as claimed in claim 2, wherein a selected workflow is taken as a basis for displaying particular work steps.

4. The method as claimed in claim 3, wherein each work step has associated tools for editing the image series or the individual images.

5. The method as claimed in claim 4, wherein the layouts are associated with the work steps automatically using a stored table.

6. The method as claimed in claim 2, wherein each work step has associated tools for editing the image series or the individual images.

7. The method as claimed in claim 1, wherein a work step includes a plurality of admissible layouts and the plurality of admissible layouts are assessed automatically in respect of their suitability for the work step on the basis of context.

8. The method as claimed in claim 1, wherein a check is automatically performed to determine whether the execution of a work step requires, is recommended to involve a layout change or may optionally involve a layout change.

9. The method as claimed in claim 1, wherein the current layout is automatically replaced by the further layout if the current layout is not one of the layouts which are admissible for the work step which is to be executed.

10. The method as claimed in claim 1, wherein a selection list with associated layouts is displayed if a plurality of layouts are admissible for the work step which is to be executed.

11. The method as claimed in claim 1, wherein the current layout is manually settable by a user.

12. The method as claimed in claim 11, wherein a manual change to the current layout involves the check being performed automatically and a result of the check being updated.

13. The method as claimed in claim 1, wherein the execution of the work step involves a result of the check being taken as a basis for at least one of essentially retaining and modifying the settings for the current layout.

14. The method as claimed in claim 1, wherein, when there are a plurality of work steps, an order for performing the work steps is stipulated by a user.

15. The method as claimed in claim 1, wherein the indicator is displayed in different colors.

16. The method as claimed in claim 1, wherein the indicator is displayed in at least one of different colors and different forms.

17. The method as claimed in claim 1, wherein other information from the data records or other data records are used for generating the image series or images.

18. A non-transitory computer readable medium including program segments for, when executed on a computer device, causing the computer device to implement the method of claim 1.

19. An apparatus for assisting the evaluation of medical image data, comprising:
- means for displaying a current layout which presents an arrangement of at least one of an image series and individual images which are generated using one or more data records;
- means for displaying at least one executable work step which has at least one associated further layout, wherein the further layout involves at least the arrangement being changed;
- means for performing a check to determine whether execution of the displayed at least one executable work step requires a layout change in which the current layout is replaced by the further layout, or whether the current layout is to be retained a result of the performed check is displayed as an indicator, the indicator indicating if the layout change is required;
- wherein, depending on whether the execution of a work step requires, is recommended to involve or may optionally involve a layout change, the indicator is displayed in different forms; and
- wherein the current layout is automatically replaced by the further layout if a layout change is assessed as being required for the execution of a work step.

* * * * *